United States Patent
Ducreux et al.

(10) Patent No.: US 8,361,798 B2
(45) Date of Patent: Jan. 29, 2013

(54) PROCESS AND INSTALLATION FOR TESTING CATALYSTS

(75) Inventors: Olivier Ducreux, Louveciennes (FR); Fabienne Le Peltier, Rueil Malmaison (FR); Cyril Collado, Lyons (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 130 days.

(21) Appl. No.: 12/668,992

(22) PCT Filed: Jun. 24, 2008

(86) PCT No.: PCT/FR2008/000890
§ 371 (c)(1),
(2), (4) Date: Sep. 29, 2010

(87) PCT Pub. No.: WO2009/016278
PCT Pub. Date: Feb. 5, 2009

(65) Prior Publication Data
US 2011/0045596 A1 Feb. 24, 2011

(30) Foreign Application Priority Data
Jul. 17, 2007 (FR) .................................... 07 05170

(51) Int. Cl.
*G01N 31/10* (2006.01)
(52) U.S. Cl. .......... 436/37; 422/129; 422/130; 422/603; 422/650; 422/652; 436/158; 436/159
(58) Field of Classification Search .................. 422/129, 422/130, 603, 650, 652; 436/37, 158–159
See application file for complete search history.

(56) References Cited

U.S. PATENT DOCUMENTS

| 3,431,077 | A | * | 3/1969 | Danforth .......................... 422/80 |
| 3,487,695 | A | * | 1/1970 | Ellis et al. .................. 73/863.81 |
| 3,787,183 | A | * | 1/1974 | Kennedy, Jr. .................... 436/37 |
| 4,397,958 | A | * | 8/1983 | Vroom .......................... 436/141 |
| 4,916,956 | A | * | 4/1990 | Semerak et al. ................ 73/863 |
| 5,287,731 | A | * | 2/1994 | Florkowski et al. ......... 73/53.05 |
| 5,304,693 | A |   | 4/1994 | Boitiaux |
| 6,495,105 | B1 | * | 12/2002 | Yamada et al. ................ 422/83 |
| 6,497,844 | B1 | * | 12/2002 | Bacaud et al. ............... 422/68.1 |
| 6,537,500 | B1 | * | 3/2003 | Brenner et al. ................. 422/88 |
| 6,548,305 | B1 |   | 4/2003 | Deves et al. |
| 6,869,800 | B2 | * | 3/2005 | Torgerson et al. .............. 436/37 |
| 7,118,917 | B2 | * | 10/2006 | Bergh et al. .................... 436/37 |

(Continued)

FOREIGN PATENT DOCUMENTS
EP 0 474 535 A 3/1992
EP 1 065 604 A 1/2001
(Continued)

*Primary Examiner* — Arlen Soderquist
(74) *Attorney, Agent, or Firm* — Millen, White, Zelano & Branigan, P.C.

(57) ABSTRACT

For testing performance levels and/ or changes over time of at least one catalyst (CAT) for a fixed-bed reactor: a device (CT) for a test, comprising at least one hollow metal cartridge (MC) containing the catalyst (CAT) is connected at a point A of an industrial chemical installation containing a reaction feedstock suitable for testing the catalyst (CAT); a liquid stream containing a fraction that is less than or equal to 1% of preheated reagents circulating in the industrial chemical installation is circulated in the cartridge (MC) through the catalyst (CAT) and sampled at a reaction temperature for a period (T), and returned to the industrial chemical installation at point B downstream of the device.

18 Claims, 3 Drawing Sheets

U.S. PATENT DOCUMENTS

| | | |
|---|---|---|
| 7,267,987 B2 * | 9/2007 | Bricker et al. .................. 436/37 |
| 2003/0118476 A1 | 6/2003 | Fujii et al. |
| 2003/0162997 A1 | 8/2003 | Fujii et al. |
| 2007/0071664 A1 | 3/2007 | Bellos et al. |

FOREIGN PATENT DOCUMENTS

| | | |
|---|---|---|
| EP | 1 258 917 A | 11/2002 |
| EP | 1 336 598 A | 8/2003 |
| FR | 2 884 443 A | 10/2006 |
| GB | 2 078 537 A | 1/1982 |

* cited by examiner

PROCESS AND INSTALLATION FOR TESTING CATALYSTS

FIELD OF THE INVENTION

The invention relates to the field for testing the effectiveness and the behavior over time of fixed-bed industrial catalysts, in particular substrate catalysts, for example balls or extrudates that most often consist of one or more catalytically active elements that are arranged on a porous substrate, for example alumina, silica-alumina, zirconia, etc. . . .

It is linked neither to a particular chemical reaction nor to a particular catalyst.

EXAMINATION OF THE PRIOR ART

The effectiveness (or the performance levels) of a fixed-bed catalyst depends on operating conditions (in particular temperature, pressure, and volumetric flow rate VVH) and can be measured according to several criteria: the conversion that is obtained for a given feedstock under given operating conditions, the selectivity of this conversion, in particular with regard to one or more desired products, and more generally the spectrum of products that are obtained.

In general, the effectiveness and the performance levels over time of a catalyst are not constant. Optionally aside from during an initial phase for initiation and steady operation where the catalyst can sometimes have increasing activity, a certain deactivation of the catalyst is noted in general over time, and said deactivation can be manifested by a loss of activity and/or selectivity, continuous or essentially asymptotic, or according to other modes of catalytic behavior. These changes of a catalyst over time can result from multiple factors that can optionally be combined. It is possible in particular to cite coking, the deposition of other impurities, for example non-limiting deposition of metals, able to plug the pores of the catalyst, reduce its surface area and/or create diffusional limitations. A catalyst can also lose active sites via different mechanisms, for example poisons of the catalyst that may or may not be reversible, and/or see its structure change, for example by a drop in the porosity and/or the surface area of the substrate.

The performance levels of a catalyst also depend on the nature of the feedstock, the presence of impurities and/or inhibiting compounds.

The manufacturers of catalysts should therefore initiate catalyst tests in the laboratory with different dimensional scales, for example on micropilot, or on a pilot of a larger dimension. It is also necessary to initiate tests of different feedstocks, with different operating conditions, comparison tests of several different catalysts, long-term tests for assessing the changes over time of the catalyst and its performance levels, etc. . . .

All of these tests are particularly expensive, both in investment, energy and feedstock consumption, etc. . . . They are conducted on test installations or "pilot installations," some of them conducting the test of a single catalyst and others the test of several catalysts that generally operate in parallel.

Typically, the analysis of the effluents of the pilot installation and often the analysis of the catalyst are carried out after a desired operating period.

These chemical analyses constitute a vast field that is well known to one skilled in the art. A large number of chemical analysis techniques are commonly used in the laboratories, for example analysis by gas phase chromatography GC or liquid phase chromatography LC, IR (infra-red) spectroscopy, SM (mass spectroscopy), NMR (nuclear magnetic resonance), "X-fluorescence," "UV fluorescence," ICP ("inductively coupled plasma," which means plasma that is coupled inductively), AA (atomic absorption), ATD-ATG (thermodifferential/thermogravimetric analysis), observation with the electronic microscope, the measurement of the BET surface area of the catalyst, etc. . . . These techniques are part of the general knowledge of one skilled in the art.

In the state of the art, however, there are no processes and devices that make it possible to significantly reduce the costs that result from the catalyst tests, in particular for the long-term tests.

SUMMARY PRESENTATION OF THE INVENTION

One object of this invention is a process for testing performance levels and/or changes over time of at least one catalyst CAT for much less expensive implementation than that of a conventional pilot installation for testing catalyst in a laboratory.

In particular, the process according to the invention makes it possible to significantly limit the necessary thermal means and the consumption of reagents.

Another object of the invention is to make possible a comparison catalyst test under conditions that are closer to those of industrial operation.

Another object of a preferred variant of the invention is to be able to carry out tests of much longer term in a more economical way, in particular with regard to the consumption of reagents.

For this purpose, the invention proposes "grafting" a CT device for testing catalyst on an industrial installation in operation and sampling a minimum fraction of the flow of reagents circulating in the industrial unit for conducting the testing of at least one bed of a catalyst CAT. The CT device can advantageously comprise at least one and preferably at least two hollow metal cartridges MC in parallel, making it possible to test two different catalysts under the same operating conditions or the same catalyst under different operating conditions.

This implementation according to the invention of a test installation connected to an existing industrial installation makes it possible to reduce the entire logistical part for providing reactive feedstock that is typically sampled under pressure and already at the reaction temperature. The testing device can then be equipped with limited thermal means, for example simple means for holding the temperature without supplying the necessary power to the heating up to the reaction temperature.

According to a preferred variant, the CT device is installed in a bypass on the industrial installation that makes it possible to reinject the CT effluents into the industrial installation. Consequently, there is no loss of reagents (feedstock), and the test can be performed with zero feedstock consumption.

The invention also relates to an industrial chemical installation that comprises a catalyst testing device that is connected to this installation. In addition, it covers several variants of such an installation, in particular when CT comprises at least two cartridges MC in parallel and/or when CT is installed in a bypass.

DETAILED PRESENTATION OF THE INVENTION

The invention proposes, more specifically, a process for testing performance levels and/or changes over time of at least one catalyst CAT for a fixed-bed reactor that comprises at least the following stages:

A device for a CT test, comprising at least one hollow metal cartridge MC that contains in particular the catalyst CAT, is connected at a point A of an industrial chemical installation that uses a reaction feedstock that is suitable for testing the catalyst CAT, At point A, a liquid stream that consists of a fraction that is less than or equal to 1% of the preheated reagents circulating in the industrial chemical installation that is circulated in the cartridge MC through the catalyst CAT is sampled at a reaction temperature for a period T, At least a fraction of the effluent of the cartridge MC is sampled for chemical analysis, Optionally, the device for the CT test of the industrial chemical installation is isolated without stopping the operation of the industrial chemical installation, and at least a fraction of the catalyst CAT is sampled for physical and/or chemical analysis.

This makes it possible to benefit from the total logistics of supplying the preheated reaction feedstock for testing performance levels and changes in the catalyst.

According to a first characteristic variant of the process according to the invention, the liquid stream is circulated in a CT device that comprises at least two cartridges in parallel, MC1 and MC2, containing different catalysts, respectively CAT1 and CAT2; identical reaction conditions for the cartridges MC1 and MC2 are maintained; and samples of separate effluents of MC1 and MC2 are taken, from which a comparative chemical analysis is carried out.

This makes it possible to be able to test two different catalysts under strictly identical conditions so as to produce a reliable comparison test.

According to a second characteristic variant of the process according to the invention, the liquid stream is circulated in a CT device that comprises at least two cartridges in parallel, MCa and MCb, containing the same catalyst CAT; different reaction conditions are maintained for the cartridges MCa and MCb; and samples of the separate effluents of MCa and MCb are taken, from which a comparative chemical analysis is produced. This makes it possible to test the influence of the operating conditions on the performance levels of the catalyst (conversion, selectivity, . . . ).

The process according to the invention also makes it possible to analyze the tested catalyst(s): The device for the CT test of the industrial chemical installation is isolated without stopping the operation of the latter; at least a fraction of the catalyst CAT, or, if necessary, at least a fraction of CAT1 and at least a fraction of CAT2 are sampled and are analyzed in the laboratory by means that are external to the CT device.

A cartridge MC can contain 2 to 5 physically separate beds in series of elementary catalysts CATi, identical or different, optionally preceded by one or more beds of guard mass(es), designed to eliminate certain impurities. This makes it possible to analyze the changes of the same catalyst at different degrees of conversion of the feedstock: the device for the CT test of the industrial chemical installation is isolated without stopping the operation of the latter, and at least a fraction of at least several—and typically all—of the elementary catalysts CATi that are analyzed in the laboratory is sampled.

The CT test device in particular can comprise an adsorbent of moisture arranged upstream from the catalyst CAT, arranged in the cartridge MC, or, if necessary, MC1 and/or MC2 and/or MCa and/or MCb, or else in at least one specific detachable cartridge WR that is arranged upstream from MC. It can also comprise several different catalysts in series.

The CT test device generally comprises heating means, and the liquid stream and/or the cartridge MC, or, if necessary, MC1 and/or MC2 and/or MCa and/or MCb are heated so as to maintain and/or obtain a suitable reaction temperature. These heating means in particular have the object of compensating for the heat losses. In some cases, additional heating power is used to test the possibility of chemical reactions with heating integrated in the reactor, or else more strict operating conditions.

According to a preferred characteristic variant of the process according to the invention, a downstream part of the CT device is connected to a point B of the industrial chemical installation for the reinjection in this installation of CT effluents, whereby CT is in a bypass between the points A and B of the industrial chemical installation. This variant has great advantages: actually, the through CT reaction batch is not lost, but is sent to the industrial installation, and therefore upgraded, which is not the case of the catalyst tests in a laboratory for which the management of the recovery of the separation of the effluents typically excludes any economical upgrading. The invention therefore also makes it possible to be able to carry out long-term tests of more than 3 months, or 6 months, or even of very long duration of more than 1 year, or two years, and even 3 years, on an actual feedstock, without particular additional expense. It is thus possible to test the long-term changes of the catalysts and their performance levels.

The invention also relates to an industrial chemical installation CIF that comprises at least one catalytic reactor R in a fixed bed that comprises a CT device for testing that is installed in a bypass between two points A and B of this installation, whereby A is located upstream or at the level of the reactor R, CT comprising at least one hollow metal cartridge MC that contains at least one catalyst CAT, and at least one sampling on the effluents of the cartridge MC and/or means for on-line analysis of these effluents, whereby the ratio of the catalytic volume of R to the catalytic volume CAT is at least 100, often at least 1,000, and generally at least 10,000. Generally, the volume of tested catalyst is very low, for example between 1 $cm^3$ and 5 liters, in particular between 10 $cm^3$ and 2 liters, and most often between 100 $cm^3$ and 1 liter, which is typically very low with regard to the catalytic volume of an industrial chemical reactor.

The CT device of the CIF installation can comprise at least one catalytic bed CAT that is different from the catalyst(s) of the reactor R, for testing, for example, another catalyst, for example a possible replacement catalyst. It can also comprise at least one cartridge MC that contains at least one catalytic bed CAT that is identical to the catalyst or to one of the catalysts of the reactor R, so as to reset the performance levels of the catalyst in the test cartridge MC with those of the industrial reactor.

The CT device of the CIF installation can also comprise at least two cartridges in parallel, MC1 and MC2, containing different catalysts, respectively CAT1 and CAT2, so as in particular to carry out reliable comparison tests under the same conditions and that operate simultaneously on the same feedstock.

The CT device of the CIF installation can also comprise at least 2 cartridges in parallel, MCa and MCb, respectively containing at least one bed of the same catalyst CAT and separate means for heating the two cartridges MCa and MCb.

The CT device of the CIF installation generally comprises means for thermal heating and means for controlling the outlet temperature of at least one metal cartridge MC, or, if necessary, MC1 or MC2 or MCa or MCb, so as to be able to maintain the temperature and/or to heat the liquid stream of the reaction feedstock. It can also comprise thermal heating means and means for monitoring the outlet temperature(s) of at least two metal cartridges in parallel: MC1 and MC2 or, if necessary, MCa and MCb. This makes it possible to be able to test different temperatures in the two parallel cartridges.

The CT device of the CIF installation can comprise at least one metal cartridge MC, or, if necessary, MC1 or MC2 or MCa or MCb in which 2 to 5 beds that are physically separate in series of elementary catalysts CATi, identical or different, are arranged. Thus, it is possible to follow the changes over time: physical changes (surface, porosity, structure, etc., . . . ) and/or chemical changes (number of active sites, etc., . . . ) of the catalyst at different successive stages of the chemical reaction.

These different beds in series of elementary catalysts CATi can each be arranged in a metal retention structure CELL that makes possible their separate extraction from the cartridge(s) MC. Each of the metal structures of retention CELL can comprise—in particular in the lower part—a permeable substrate of the corresponding CAPTI mass, a ring section with a diameter that is less than the inside diameter of the corresponding cartridge MC, and a means for limiting the bypass flow around this ring section.

It is also possible to arrange the different elementary catalysts CATi between inert balls, for example, of carborundum, or between ceramic fibrous layers, for example of quartz wool, or to separate them by any other suitable means.

Figure 1:
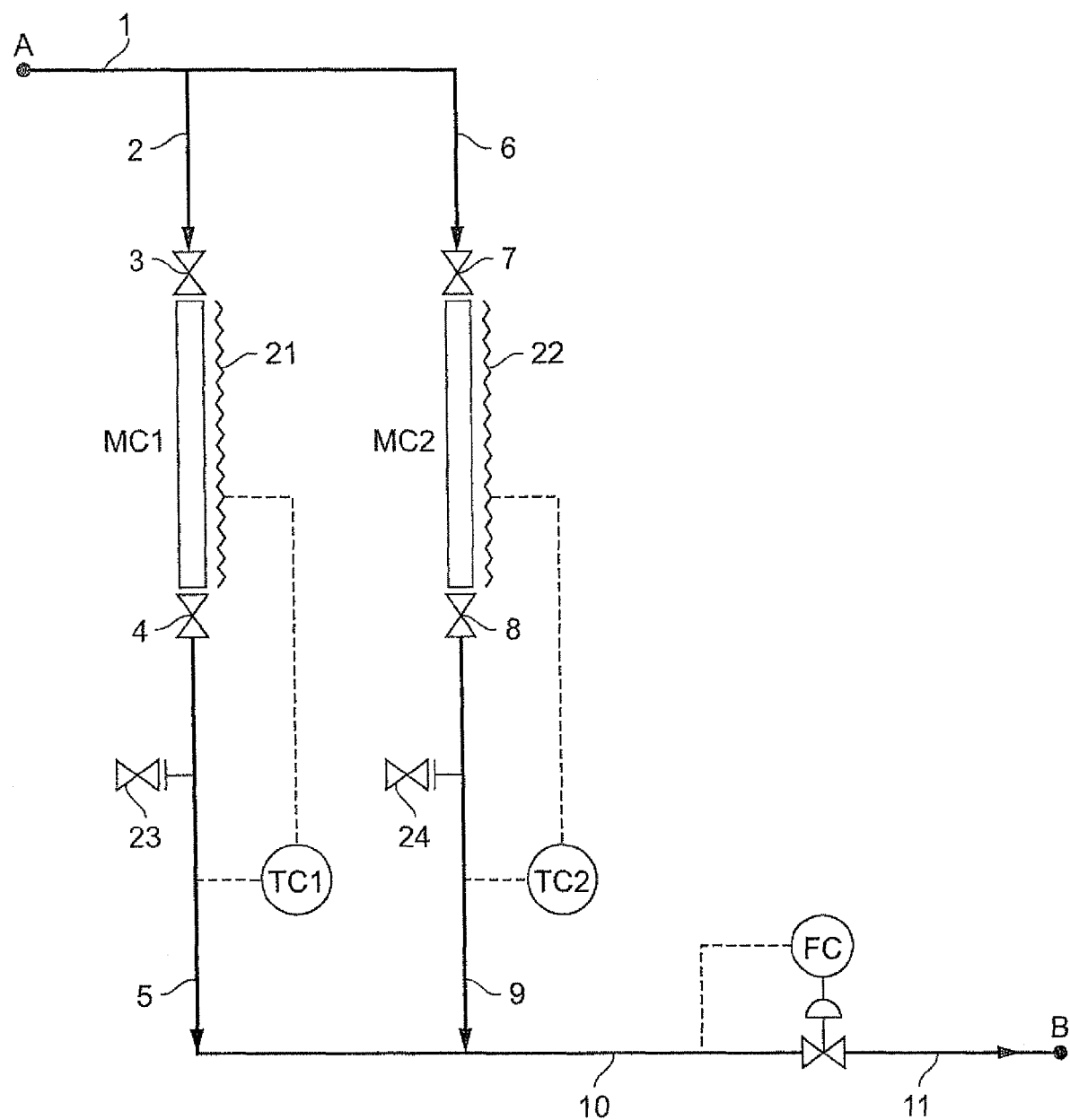
FIG. 1 schematically shows a CT device that can be used for the implementation of the process according to the invention.

Reference is now made to FIG. 1:

The device comprises a line 1 for feeding a liquid stream that is sampled at a point A in a reaction feedstock of an industrial chemical reactor R. The feed line is subdivided into two branches 2, 5 and 6, 9, each comprising a detachable, hollow metal cartridge, respectively MC1 and MC2, which can be isolated between two valves, respectively 3, 4 and 7, 8. These cartridges are filled with several successive layers of catalyst. For example, the cartridge 4a contains 3 successive layers of a first catalyst CAT1 that is identical to the industrial catalyst of the reactor R, and the cartridge 4b contains 3 successive layers of a second catalyst CAT2 that it is desired to evaluate as a replacement catalyst.

Upstream, each of these two cartridges can optionally comprise one or more guard mass(es) that are designed to protect the catalysts CAT1 and CATb against poisons of these catalysts (water, mercury, H2S, etc. . . . ).

The sampled reaction liquid stream therefore reacts on the two catalysts CAT1 and CAT2 in parallel. Two heating resistors 21 and 22 that are controlled by means for monitoring temperature TC1 and TC2 make it possible to heat the cartridges MC1 and MC2 separately to maintain the temperature and/or to obtain independently the desired outlet temperatures of the two effluents of these catalytic cartridges. Two samplings 23 and 24 make it possible to take samples of the effluents of MC1 and MC2 for comparative chemical analysis.

Downstream, the effluents of MC1 and MC2 are combined and circulate in a line 10 whose flow rate is monitored by means FC for monitoring flow rate. The effluents are then evacuated via the line 11 to point B that is, for example, the connecting point downstream from the industrial reactor R. It is also possible to monitor the flow rates separately in the cartridges MC1 and MC2, for example by means that are not shown, such as manual or regulation control valves so as to ensure identical flow rates. This installation operates as it was already explained above by making it possible to test different catalysts under the same conditions. If CAT1 is identical to CAT2, it is also possible to test the influence of different operating conditions, such as the volumetric flow rate and/or the temperature. Finally, it is clear that it is possible to take samples from the catalysts that are tested for physical and/or chemical analysis, without stopping the industrial installation CIF and the reactor R.

Figure 2:
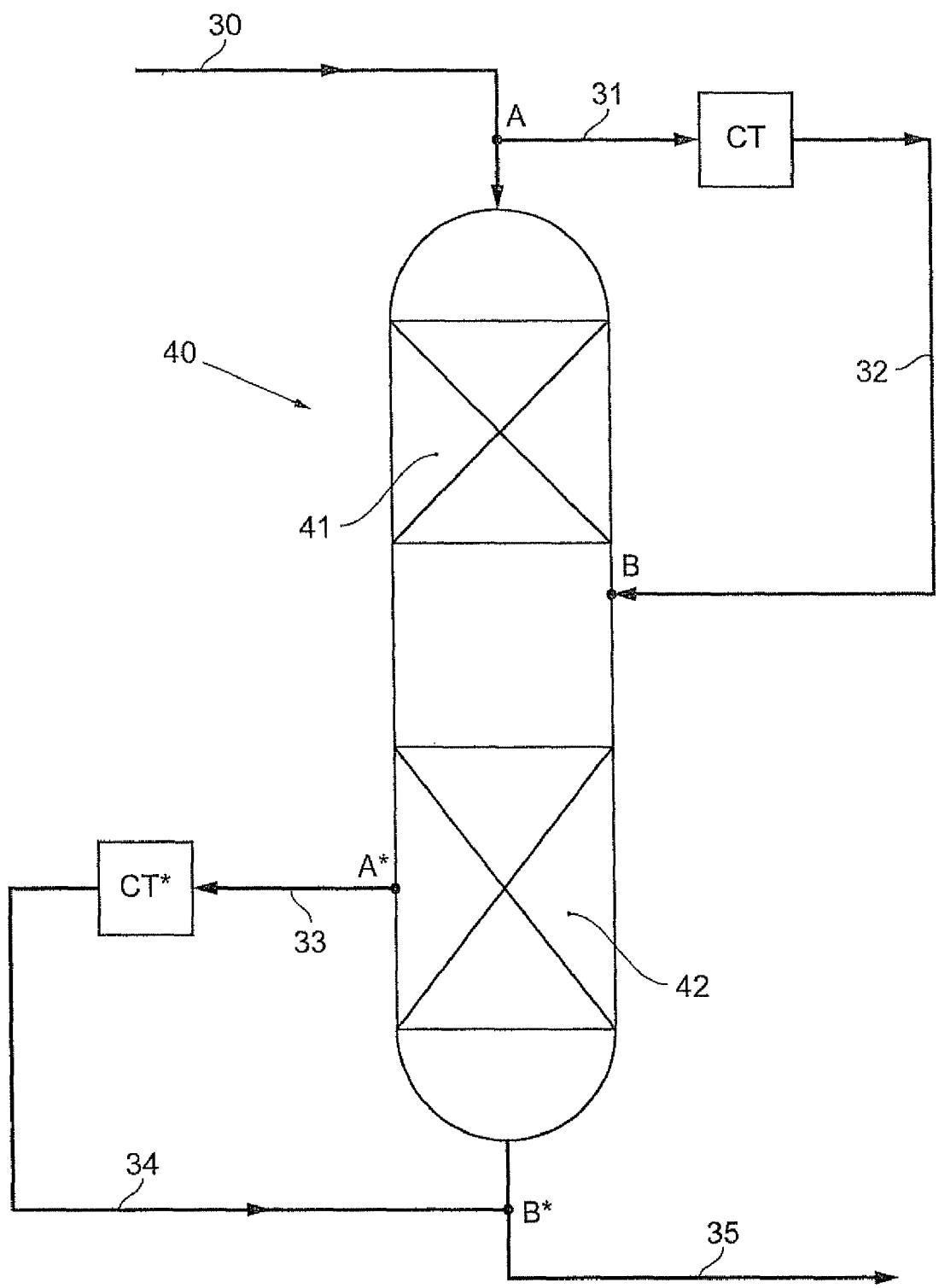
FIG. 2 schematically shows a reactor of an industrial chemical installation CIF that is equipped with two bypass devices CT and CT* that are used for the implementation of a variant of the process according to the invention.

Reference is now made to FIG. 2. Two devices CT and CT* are installed in a bypass at several points around and at the level of a chemical reactor 40 that comprises two catalytic beds 41 and 42. The reactor 40 is fed by a liquid stream (reagents) from a line 30, and the effluent of the reactor is evacuated via the line 35.

The first catalyst testing CT device, the most upstream, is connected at a point A upstream from the reactor, and a very small fraction of the liquid stream (for example, less than 1/1,000 or 1/100,000 of the total liquid circulating in the industrial unit, for example, between 1/1,000 and 1/1,000,000 of the total liquid) is sampled, fed in a CT bypass via the line 31, passes through CT, and the CT effluent is reinjected via the line 32 into the reactor at a point B that is located between the two catalytic beds 41 and 42.

The second catalyst testing CT* device, the most downstream, is connected at an intermediate point A* of the second catalytic bed 42, and a very small fraction of the reaction liquid stream (for example less than 1/1,000 or 1/10,000 of the total liquid) is sampled, fed in a CT* bypass via the line 33, passes through CT*, and the CT* effluent is reinjected via the line 34 at a point B* that is located on the outlet line 35 of the reactor 40.

In this configuration, it is possible to test both catalysts for replacement of the industrial catalyst of the first catalytic bed 41, by the catalyst(s) tested in CT, and those that can replace the industrial catalyst of the end of the second catalytic bed 42, whereby the latter are tested in CT*.

More generally, it is possible to use several CT bypass devices.

Figure 3:
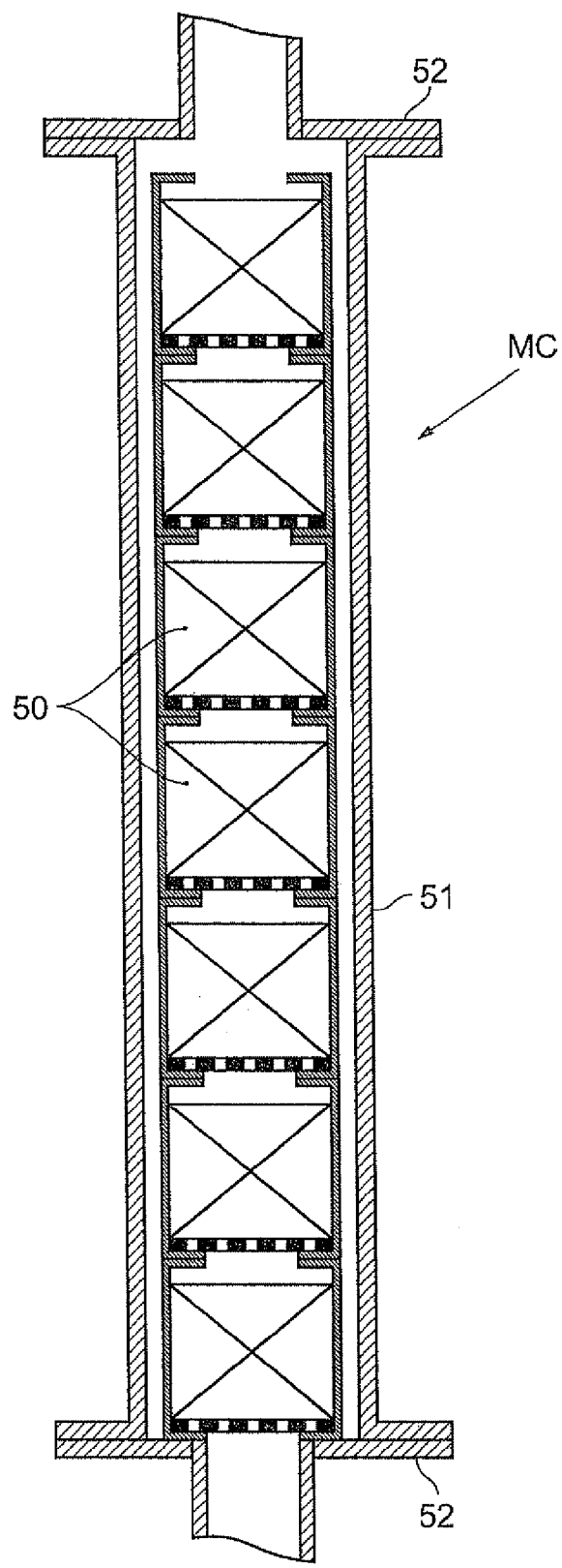
FIG. 3 schematically shows a preferred cartridge MC of a CT device that can be used for the implementation of the process according to the invention.

Reference is now made to FIG. 3 that shows a recovery cartridge MC of one of the preferred types according to the invention. This cartridge comprises an elongated cylinder 51 that contains several successive catalysts in series 50 (and optionally recovery masses for protection upstream), physically separate and able to be stacked on one another, to form the overall recovery mass. Each catalyst is arranged in a basket that comprises a grid or a piece of perforated sheet metal in the lower part, with an opening size that is small enough so that the catalyst grains do not pass through.

The baskets are typically self-supporting, which allows their overall stacking. The lower edge of a basket rests on the upper edge of the basket immediately below. The upper edge of a basket is furthermore used advantageously for its gripping and its extraction from the cartridge MC.

The baskets can be machined to allow only a minimum play with the metal ring of the cartridge MC. It is also possible to arrange a seal (not shown in FIG. 3), for example a braid around each basket, to prevent the bypassing of the catalyst by a portion of reaction fluid. The cartridge also comprises two detachable flat bottoms 52 that make possible the extraction of the baskets.

The invention is not limited to the means that are explicitly described and can comprise any characteristic that is already known in the fields for testing catalysts and for the analysis of chemical compounds.

The invention claimed is:

1. A process for testing performance levels and/or changes over time of at least one catalyst for a fixed-bed industrial chemical reactor installation having
a bypass between a point that a reaction feedstock has been preheated and a point downstream therefrom, said process comprising:
connecting a connectable and disconnectable catalyst testing device in said bypass, the catalyst testing device comprising at least one hollow metal cartridge containing catalyst,
circulating a liquid stream comprising less than or equal to 1% of the preheated reaction feedstock through the catalyst in the at least one cartridge at reaction conditions for a period of time to produce at least one effluent and reinjecting the at least one effluent into the industrial chemical reactor installation,
subjecting at least a fraction of the at least one effluent from the at least one cartridge to chemical analysis, and
isolating the catalyst testing device in the bypass from the industrial chemical reactor installation after the period of time without stopping operation of said industrial chemical reactor installation, and sampling at least a fraction of the catalyst for physical and/or chemical analysis.

2. A process according to claim 1, in which said catalyst testing device comprises at least two cartridges in parallel containing catalyst.

3. A process according to claim 2, in which the at least two cartridges contain different catalysts, maintaining the cartridges at identical reaction conditions to produce at least two effluents and taking samples from each effluent to produce comparative chemical analysis.

4. A process according to claim 2, in which the at least two cartridges contain the same catalyst, maintaining the cartridges at different reaction conditions to produce at least two effluents and taking samples from each effluent to produce comparative chemical analysis.

5. A process according to claim 2, wherein at least a fraction of each catalyst is sampled and analyzed by means that are external to the catalyst testing device.

6. A process according to claim 1, wherein said at least one cartridge contains two to five physically separate catalyst beds in series, the catalyst in the beds being identical or different, optionally preceded by one or more guard mass beds and at least a fraction of at least several of the catalysts are sampled for analysis.

7. A process according to claim 1, in which said catalyst testing device further comprises a moisture adsorbent arranged upstream from the at least one catalyst in the at least one cartridge.

8. A process according to claim 1, in which said catalyst testing device further comprises heating means to maintain and/or to obtain a reaction temperature.

9. An industrial chemical reactor installation comprising:
at least one fixed-bed catalytic reactor, a bypass in the industrial chemical reactor installation between a point that a reaction feedstock has been preheated and a point downstream therefrom, a connectable and disconnectable catalyst testing device installed in said bypass,
said catalyst testing device comprising at least one hollow metal cartridge containing at least one catalyst, and at least one sampling means for sampling effluents from the at least one cartridge for analysis, wherein a ratio of the catalytic volume of the reactor to the catalytic volume of the at least one catalyst testing device is at least 100.

10. An industrial chemical reactor installation according to claim 9, in which the catalyst in the at least one cartridge of the catalyst testing device includes at least one catalytic bed with a catalyst that is different from the catalyst in the reactor.

11. An industrial chemical reactor installation according to claim 9, in which the catalyst in the at least one cartridge of the catalyst testing device includes at least one catalytic bed with a catalyst that is identical to the catalyst in the reactor.

12. An industrial chemical reactor installation according to claim 9, wherein the catalyst testing device comprises at least two cartridges in parallel containing different catalysts.

13. An industrial chemical reactor installation according to claim 12, wherein the catalyst testing device comprises thermal heating means and means for monitoring the outlet temperature of the at least two cartridges.

14. An industrial chemical reactor installation according to claim 9, wherein the catalyst testing device comprises at least two cartridges in parallel containing at least one bed of the same catalyst in each cartridge and separate means for heating the at least two cartridges.

15. An industrial chemical reactor installation according to claim 9, wherein the catalyst testing device comprises thermal heating means and means for monitoring the outlet temperature of the at least one cartridge.

16. An industrial chemical reactor installation according to claim 9, in which the at least one cartridge contains two to five physically separate catalyst beds in series, the catalyst in the beds being identical or different.

17. An industrial chemical reactor installation according to claim 16, in which said catalyst beds are each arranged in a metal retention structure that allows separate extraction of the catalysts from the at least one cartridge.

18. An industrial chemical reactor installation according to claim 17, in which each of the metal retention structures comprises a permeable substrate for holding a mass of catalyst, a ring section with a diameter that is less than an inside diameter of the at least one cartridge and a means for limiting the bypass flow rate around the ring section.

* * * * *

UNITED STATES PATENT AND TRADEMARK OFFICE
CERTIFICATE OF CORRECTION

PATENT NO.       : 8,361,798 B2					Page 1 of 1
APPLICATION NO. : 12/668992
DATED            : January 29, 2013
INVENTOR(S)      : Ducreux et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 385 days.

Signed and Sealed this
First Day of September, 2015

Michelle K. Lee
*Director of the United States Patent and Trademark Office*